United States Patent
Vogel

(10) Patent No.: US 9,524,623 B2
(45) Date of Patent: Dec. 20, 2016

(54) METHOD AND DEVICE FOR INDICATING AUTOMATICALLY IDENTIFIED FLAWS

(75) Inventor: Kai Vogel, Seeheim-Jugenheim (DE)

(73) Assignee: VIPROTRON GMBH, Darmstadt (DE)

( * ) Notice: Subject to any disclaimer, the term of this patent is extended or adjusted under 35 U.S.C. 154(b) by 603 days.

(21) Appl. No.: 13/876,307

(22) PCT Filed: Sep. 27, 2011

(86) PCT No.: PCT/EP2011/066728
§ 371 (c)(1),
(2), (4) Date: Apr. 14, 2013

(87) PCT Pub. No.: WO2012/041830
PCT Pub. Date: Apr. 5, 2012

(65) Prior Publication Data
US 2013/0194102 A1 Aug. 1, 2013

(30) Foreign Application Priority Data
Sep. 27, 2010 (DE) .................... 10 2010 037 788

(51) Int. Cl.
*G08B 7/00* (2006.01)
*G08B 21/00* (2006.01)
(Continued)

(52) U.S. Cl.
CPC .............. *G08B 5/36* (2013.01); *G01N 21/958* (2013.01); *G01N 2021/8861* (2013.01); *G01N 2021/9586* (2013.01)

(58) Field of Classification Search
CPC ........... G08B 5/36; G08B 7/066; G01N 21/86; G01N 21/00; G01N 21/9501; G01N 21/958; G01N 21/89; G01N 21/90; G06K 13/067; G06T 7/0004
(Continued)

(56) References Cited

U.S. PATENT DOCUMENTS 4,483,615 A * 11/1984 Bieringer ............. G01N 21/896
209/526
4,581,939 A * 4/1986 Takahashi .......... G01N 29/2418
356/432
(Continued)

FOREIGN PATENT DOCUMENTS

DE 3325125 C1 2/1985
DE 4307590 C2 9/1994
(Continued)

OTHER PUBLICATIONS

German Official Action (Jul. 25, 2011) from corresponding German App. DE 10 2010 037 788.0 (with machine translation).
(Continued)

*Primary Examiner* — George Bugg
*Assistant Examiner* — Munear Akki
(74) *Attorney, Agent, or Firm* — WRB-IP LLP

(57) ABSTRACT

A method is provided for indicating automatically identified flaws on or in a test specimen. A location of a defect on or in a test specimen identified by an inspection unit is subsequently indicated. A lighting unit, for example color LEDs, is used to generate an illuminated indicator marking the location of the defect on the surface or on at least one adjoining lateral edge of the test specimen. After the automatic identification of the flaw, it is checked on the basis of quantifiable properties of the defect whether the defect meets a predefinable quality criterion, and an illuminated indicator marking the location of the defect at or on the test specimen is generated only if the quality criterion is not met. The coloring of the marking illuminated indicator is predefined depending on quantifiable properties of the defect.

14 Claims, 2 Drawing Sheets

(51) Int. Cl.
  *G01N 21/86* (2006.01)
  *G06K 9/00* (2006.01)
  *G01N 21/84* (2006.01)
  *G08B 5/36* (2006.01)
  *G01N 21/958* (2006.01)
  *G01N 21/88* (2006.01)

(58) Field of Classification Search
  USPC ....... 340/691.1, 559.4, 329, 674; 250/559.4; 356/239.1, 239, 429, 430.237; 382/141, 382/142
  See application file for complete search history.

(56) References Cited

U.S. PATENT DOCUMENTS

| | | | | |
|---|---|---|---|---|
| 4,665,392 | A * | 5/1987 | Koontz | G06K 7/14 250/223 R |
| 5,046,110 | A * | 9/1991 | Carucci | G03F 7/7065 348/126 |
| 5,280,374 | A * | 1/1994 | Nakai | G02F 1/1309 349/192 |
| 5,459,330 | A | 10/1995 | Venaille et al. | |
| 5,691,811 | A * | 11/1997 | Kihira | G01N 21/896 356/239.1 |
| 5,870,204 | A * | 2/1999 | Chiu | G01N 21/8903 356/430 |
| 5,987,159 | A * | 11/1999 | Nichani | G01N 21/88 382/141 |
| 6,618,495 | B1 * | 9/2003 | Furnas | G01N 21/90 209/526 |
| 7,592,616 | B1 * | 9/2009 | Velidandla | C30B 29/36 250/559.29 |
| 8,306,308 | B2 * | 11/2012 | Choi | G01N 21/952 356/601 |
| 2002/0005892 | A1 * | 1/2002 | Herre | G01N 21/8806 348/86 |
| 2004/0179193 | A1 * | 9/2004 | Maezono | G01N 21/896 356/239.1 |
| 2006/0124872 | A1 * | 6/2006 | Gerard | G01N 21/90 250/559.4 |
| 2006/0280356 | A1 * | 12/2006 | Yamagishi | G09G 3/006 382/141 |
| 2007/0171661 | A1 * | 7/2007 | Desvaud | G01N 21/8901 362/458 |
| 2010/0149327 | A1 * | 6/2010 | Okamura | G01N 21/896 348/88 |
| 2011/0091093 | A1 * | 4/2011 | Yang | G06T 7/001 382/141 |
| 2011/0221885 | A1 * | 9/2011 | Suzuki | G01N 21/21 348/125 |

FOREIGN PATENT DOCUMENTS

| | | |
|---|---|---|
| DE | 20004332 U1 | 8/2000 |
| DE | 10111409 A1 | 9/2001 |
| DE | 102006014345 B3 | 8/2007 |
| JP | 2006066344 A | 3/2006 |
| WO | WO 2010058759 A1 * | 5/2010 |

OTHER PUBLICATIONS

International Search Report (Jan. 18, 2012) for corresponding International Application PCT/EP2011/066728.

* cited by examiner

METHOD AND DEVICE FOR INDICATING AUTOMATICALLY IDENTIFIED FLAWS

BACKGROUND AND SUMMARY

The invention relates to a method for indicating automatically identified flaws on or in a test specimen, wherein a location of a defect on or in a test specimen identified by an inspection unit is subsequently indicated.

As part of the continual advance in the automation of industrial manufacturing processes, more and more individual manufacturing processes or production and processing steps are performed automatically. At the same time the attempt is also made to automate in large part or completely the inspection of the individual manufacturing and production steps as well as any required final inspection of the manufactured product. In many sectors it is possible using appropriate sensors and measuring devices to ensure a meaningful and reliable quality control that is comparable and even superior to a manual check or inspection.

However, practice has shown that there are also manufacturing processes or products for which an automated flaw detection and quality inspection are not possible or are possible to only a limited extent. In many such cases a manual check and inspection of the manufacturing steps or of the product in question are performed during or after the manufacturing process.

In practice it is known to identify defects and their location on the surface of or even within a test specimen using an inspection unit, in order to aid in or in preparation for a manual check of a test specimen, insofar as the specimen comprises or consists, for example, of glass or some other transparent material. The identified flaws are subsequently indicated by means of a display device. In addition to simple display devices that are merely capable of indicating the presence of a defect, for example, by a red illuminating signaling device, screen displays are also known from practice that are capable of reproducing schematically an image of the test specimen and the location of the detect on the surface of the test specimen identified by the inspection unit. This makes it easier to locate the defect on the test specimen, so that the required manual inspection of the defect can be performed and completed more quickly.

Manual checks and quality inspections of this type are also performed, for example, during the manufacture of individual glass panes and the further processing thereof into an insulating glass product. Reliably differentiating between defects, such as for example, bubbles, scratches, coating or film defects on the one hand, and adhering dust or dirt particles, or removable impurities on the other hand is nearly impossible using economically viable automatic inspection devices. If a flaw is identified, it usually requires a manual inspection to decide whether it is an irreparable defect or merely an impurity that can be eliminated. Where large surfaces are involved, such as in the case of large window panes or glass doors, locating a defect may take considerable time, even when its location on the glass pane is indicated schematically on a monitor arranged next to the glass pane.

In the manufacture of motor vehicles it is known to mark a defect identified by an automatic inspection unit using a washable coloring in order to quickly locate the defect further along on the production line and to eliminate it if possible. Color marking is usually performed by robots, which requires a complex control system. In the case of an early manual inspection, applying a color marking and subsequently quickly removing it involves frequently unnecessary effort and high costs.

It is also known to use color marking in the manufacture of raw glass in order subsequently to be able to remove the color marked glass plates from the production process. The application of color marking in this case is expensive as well. To the extent that it involves a removable impurity, removal of the marking in order to be able to continue to use the glass plate is very time-consuming.

Therefore, it is desirable to improve a method for indicating flaws that have been automatically identified, thereby making it easier to locate the flaws on the surface of the test specimen in order to enable a quick and reliable manual inspection of the flaw.

According to an aspect of the invention a lighting unit is used to generate an illuminated indicator which marks the location of the defect on the surface of the test specimen, behind the test specimen or in the area of at least one adjoining lateral edge of the test specimen. Because the illuminated indicator generated by the lighting unit indicates the location of the defect directly on the surface or on the lateral edges of the test specimen, it is possible to locate the flaw both quickly and reliably. For example, the lighting unit can generate an illuminated indicator on the snake of the test specimen which illuminates a small definable area of the surface of the test specimen in which the defect is located. Repeated comparisons of the surface of the test specimen with a defect marking in an image on a screen located nearby, as is known in conjunction with inspection units of the prior art, and which has become necessary in particular for locating an oftentimes small defect on large surfaces of a test specimen, are no longer required.

If, for example, due to spatial conditions or to the material of the test specimen, it is not possible to generate an illuminated marking on the surface of the test specimen, or it involves disproportionately high costs, the location of the defect can, for example, be indicated along the lateral edges of the test specimen by means of laterally arranged light rails. The light rails can also be arranged in the area of the lateral edges of the test specimen behind the test specimen or offset from the test specimen, in order to allow the test specimen to be easily transported, for example, within a production line, or in order to be able to easily integrate the light rails in the production line.

It is also conceivable in the case of a transparent test specimen to generate an illuminated marking directly behind the test specimen against a suitable background or against an area lighting unit such that the defect is located directly in front of the illuminated marking in the test specimen and can be quickly located for a manual check.

Depending on the circumstances the marking illuminated indicator can ensure the desired location information by targeted bright illumination of the location of the defect. The marking illuminated indicator may also be predefinably offset on the surface of the test specimen relative to the location of the defect in the event direct illumination of the defect makes a manual check thereof more difficult. It can also be expedient for the marking illuminated indicator to fully or at least partially illuminate the surface of the test specimen with merely a small area around the automatically identified flaw being darkened.

In accordance with an embodiment of the inventive concept, it is provided that multiple flaws are indicated simultaneously, successively or alternatingly with the marking illuminated indicator. The illuminated indicator can be selectively switched between multiple flaws, either manually or automatically, that is, at predefined intervals. To allow for an intensive inspection, a manual selection of the defect marked by the illuminated indicator can be expediently predetermined at any time.

It is also conceivable that the illuminated indicator can detect multiple test specimens simultaneously and identify any flaws in all of the detected test specimens simultaneously, successively or alternatingly. To the extent deemed sufficient in individual cases, it is also possible to mark just a single detective test specimen and, for example, to label it for isolating or singling out.

To be able to easily adapt the effort expended on the manual check and inspection to the predefined requirements and quality criteria in each individual case, it is provided that after automatic identification of the flaw it is checked on the basis of quantifiable properties of the defect whether the test specimen, despite the defect, meets a predefinable quality criterion, and that an illuminated indicator marking the location of the defect at or on the test specimen is subsequently generated only if the quality criterion is not met.

According to an aspect of the invention, manually checking the defect and subsequently deciding what is to be done further with the defective test specimen can be facilitated in that an expansion and/or orientation of a non-radially symmetrical marking illuminated indicator is predefined depending on the quantifiable properties of the defect. Thus, for example, it is possible to display the automatically identified type or size of defect by way of the diameter of a circular illuminated spot predefined in accordance with said defect. It is equally conceivable and in practice often helpful if an elongated defect such as, for example, a scratch is marked, for example, by a linear or elliptically shaped illuminated indicator adapted to the former. The orientation of the non-radially symmetrical illuminated indicator can advantageously match the orientation of the defect on the surface of the test specimen.

It is expediently provided that a coloring of the marking illuminated indicator is predefined depending on quantifiable properties of the defect. For example, defects that are not considered critical can be marked by a green or blue illuminated spot. A defect that is classified as critical based on type or size and which, for example, could result in the test specimen being rejected, can be marked in red or in another striking and, if appropriate, cautionary signal color.

It is also conceivable that the marking illuminated indicator flashes or migrates across a predetermined area of the surface of the test specimen.

If additional information is available that appears relevant or should be considered in connection with a manual check and inspection, it is alternatively or additionally possible using the marking illuminated indicator to identify further properties of the test specimen. In this way it is possible, for example, to indicate deviations in the material composition or shape of the test specimen. It is also conceivable to mark predetermined areas for which different quality criteria apply and which must be considered in connection with the manual check.

It is further possible using the illuminated indicator to indicate whether the test specimen meets predefined requirements, for example, with respect to its size or quality. Thus, for example, when using light rails for marking a defect, each of the light sources projecting above the test specimen can be used to indicate the target size or, based on the color of the light source, the quality of the test specimen. The light rails can also be employed as a positioning aid or as a control.

It is equally conceivable to use the illuminated indicator to indicate zones on the test specimen that differ in quality. Thus, respective areas with different quality requirements can be indicated with different colors to thereby further facilitate the manual check and inspection of defects.

To make it possible to aid a manual check even in the case of continuously moving test specimens, it is provided that the marking illuminated indicator is carried along with the moving test specimen.

The present invention also relates, according to an aspect thereof, to a device for indicating automatically identified flaws on a surface of a test specimen. According to an aspect of the invention, the device includes a positioning means for the test specimen and a lighting unit by means of which an illuminated indicator marking the location of the defect on the surface or at least on one adjoining lateral edge of the test specimen is generated. The lighting unit is in a predefinable position or spatial relation with respect to the positioning means, so that for a position and orientation of the test specimen predefined by the positioning means, the location of a defect on the surface of the test specimen can be reliably and precisely marked by the lighting unit.

The positioning means can include, for example, a stop capable of being relocated in the transport path of the test specimen or a receptor device for the test specimen, so that the test specimen can be arranged or fixed in a predefined position for as long as the defect is indicated. If, for example, the defect should be indicated immediately subsequent to the production of the specimen when being transported on a conveyor device, a belt or roller conveyor as the case may be, the positioning means can comprise a stop sensor which halts the conveyor device as soon as a test specimen has reached a position predetermined for defect indication.

In the event the test specimen is not halted during transport, or the test specimen cannot be halted and positioned with the required accuracy, the conveyor means in conjunction with position detection devices can serve as a positioning means. For example, the respective position of the test specimen can be detected by means of suitable detectors or an optical camera system and can be communicated to the lighting unit or be taken into account by the latter. The current position is detected by the positioning means and taken into account with respect to the defect indication, which is adapted to the movement of the test specimen and which generates subsequent to the test specimen a site-correlated indicator of the identified defect or multiple defects.

Positioning means is understood in the following to encompass all those devices with which the position of the test specimen can be predefined or detected in order together with the lighting unit to allow a defect to be indicated on or at the test specimen.

According to an advantageous embodiment of the inventive concept, it is provided that the lighting unit comprises at least one light rail having multiple, serially arranged light sources. Light rails with a large number of adjacently arranged LEDs can be produced cost-effectively or purchased preassembled. Based on the position of an illuminating light source within a light rail, it is possible to demarcate and quickly check manually a corresponding strip-like area of the surface of the test specimen.

It is advantageous to use laterally arranged light rails, in particular in conjunction with test specimens made of a transparent material, such as for example, glass panes, in which generating an illuminated marking on the surface of the glass pane is not possible or possible only with considerable structural outlay.

Preferably, the lighting unit includes two light rails arranged substantially perpendicular to one another, each including multiple, serially arranged light sources. The two light rails arranged at a right angle arranged angle to one another makes it easier to locate a flaw on a rectangular surface bounded by the light rails. The size of the surface area of the test specimen marked or illuminated by the light sources in the light rails that are conveniently activated and lit, also depends on the number of or on the spacing between the light sources in the light rails, as well as on the distance of the flaw on or in the test specimen relative to the light rails. It has been shown that in many cases involving light rails in which the serially arranged light sources are spaced approximately 1 cm apart, it can be made much easier to locate a flaw.

It is equally conceivable that in particular in test specimens non-rectangular in shape, the two or more light rails are arranged not perpendicular to one another but rather, for example, at an angle to one another and aligned so that the progression of the light rails is adapted to the contours of the test specimen.

According to another embodiment of an aspect of the inventive concept, it is provided that the lighting unit includes at least one pivotable or movable light source arranged at a distance from the test specimen. By suitably controlling the orientation of the light source, it is possible to position the illuminated marking generated by the light source anywhere on the surface of the test specimen. It is even possible to track without great difficulty the marking illuminated indicator on a moving test specimen. Multiple pivotable or movable light sources can be provided. The multiple light sources can be used to mark multiple defects simultaneously. It may also be expedient to subdivide the space detectable for marking a flaw among multiple light sources in order to facilitate control thereof and to accelerate the individual marking of a detect located in the respective, corresponding area. The at least one light source can be both pivotably and movably arranged.

It is also possible to indicate simultaneously any occurring defects as well as other properties in multiple test specimens being transported simultaneously adjacent one another, in particular, but not only when using multiple light sources.

The lighting unit may also comprise an area light sources composed of or comprising multiple separately controlled segments that correspond to individual areas of the surface or to a cross-sectional area of the test specimen. It is preferable if the test specimen consists of or comprises a transparent material with the surface thereof located immediately adjacent the area light source, so that each area of the surface of the test specimen can be illuminated by an associated segment of the area light source.

The area light source may comprise or consist, for example, of an LED matrix, the light surface of which can correspond to the test specimen and on which a defect in the test specimen can be indicated by a spatially correlated illuminated indicator in the LED matrix. The LED matrix can be advantageously arranged behind a test specimen made of a transparent material that is passed in front of the light source, such that the illuminated indicator can be observed through the test specimen and generates an immediate indication of the location of the defect. Such a lighting unit embodiment can be advantageously used in conjunction with the manual check and inspection of glass panes.

The area light source can also be arranged separately from the test specimen, in which case a correlation traceable to the observer is to be ensured between the illuminated indicator and the defect on the test specimen. It is also conceivable for an area light source to be defined by multiple light rails arranged separately and parallel to one another.

According to an embodiment of the inventive concept it is provided that the light source is capable of generating an illuminated marking that is predefinable with respect to its shape and size. For this purpose the light source can include a controllable focusing device which can be used to predefine and vary the expansion and optionally also the shape of the illuminated marking on the surface of the test specimen or on an illuminated screen located directly nearby. It is also conceivable to predefine the size and shape of the marking illuminated indicator using suitable apertures that can be arranged in the luminous cone of the light source.

It is preferable if the light source is able to generate an illuminated marking in different colors. Characteristics of the defect identified in advance can be signaled by different colors of the illuminated marking and in this way can easily be taken into account in a subsequent manual check.

BRIEF DESCRIPTION OF THE DRAWINGS

Exemplary embodiments of the inventive concept shown in the drawing are described in greater detail below. In the drawings.

DETAILED DESCRIPTION

Figure 1:
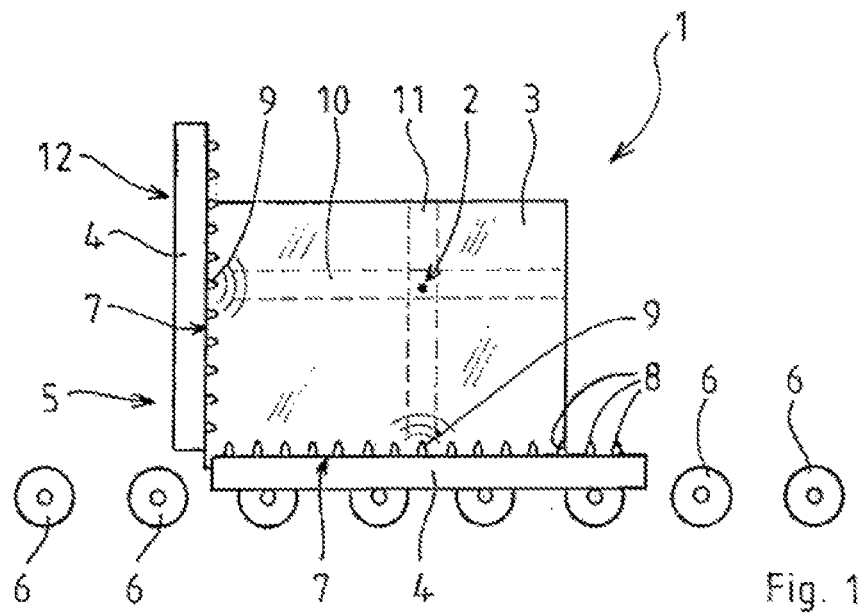
FIG. 1 shows a schematic view of a device for indicating flaws on a surface of a glass pane, wherein the device includes two light rails arranged at right angles to one another with multiple serially arranged light sources.

FIG. 1 is an exemplary and merely schematic view of a device 1 for indicating automatically identified defects 2 in a glass pane 3. In this exemplary embodiment the glass pane 3 is the test specimen that previously underwent an automatic investigation for flaws.

Two light rails 4 are arranged perpendicular to one another along a production line 5 indicated merely schematically by multiple transport rollers 6 arranged in a row, thereby enabling the glass pane 3 during transport along the production line 5 to be arranged or positioned with its lateral edges 7 in alignment with the light rails 4. The light rails 4 may also exhibit a small lateral or perpendicular offset in relation to the glass pane 3, where this seems expedient, for example, for transporting the glass pane 3 in the production line 5 or for simple integration in the production line 5. However, the offset must not be so great that it makes it more difficult to rapidly associate the illuminated marking generated by the light rails 4 with a flaw on or in the glass pane 3.

Each of the light rails 4 includes multiple, serially arranged light sources 8. The light sources are colored LEDs which can be controlled individually by means of a suitable control device. It is also feasible to use monochromatic LEDs when no other information beyond the location of the defect 2 is intended to be signaled by different colored LEDs.

To make it easier to locate the defect 2 in the glass pane 3 prior to a manual check and inspection, the LEDs 9 that are closest both horizontally and vertically to the defect are illuminated. The defect 2 is then located in a cross section of the linear or column-shaped areas 10, 11 predefined by the two illuminated LEDs 9. The light rails 4 together with the light sources 8, 9 define a lighting unit 12 with which the location of the defect 2 can be identified at the lateral edges 7 of the class pane 3.

Figure 2:
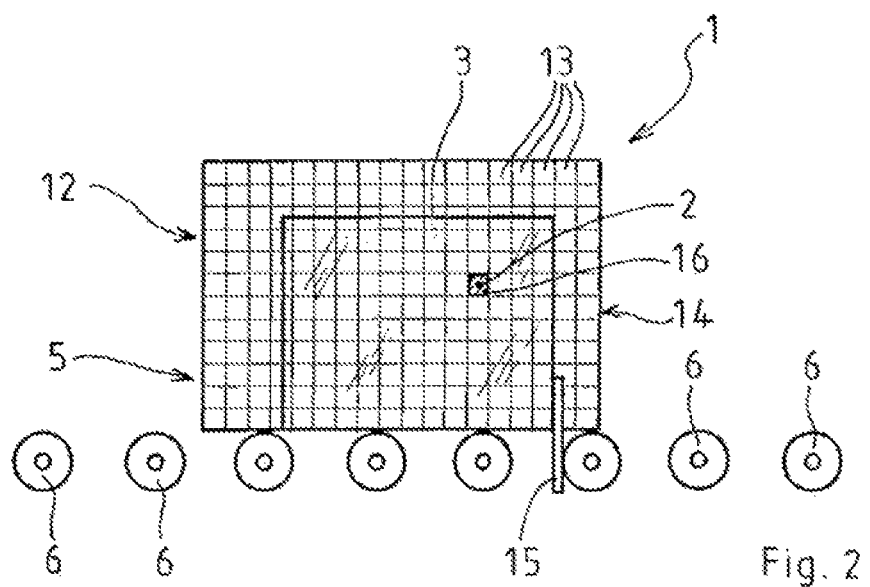
FIG. 2 shows a device with a lighting unit that includes an area light source composed of or comprising multiple separately controllable segments, FIG. 3 in turn shows a differently designed device with a pivotable light source located at a distance from the test specimen.

In the exemplary embodiment also shown schematically in FIG. 2, the device 1 includes a differently designed lighting unit 12 that consists of or comprises an area light source 14 composed of or comprising multiple, separately controllable rectangular segments 13. The individual segments 13 can be illuminated separately. Placing the glass pane 3 directly in front of the area light source 14 makes it easier when illuminating a segment 16 or multiple segments 16 behind the glass pane 3 to quickly locate a defect 2 or multiple defects 2 in the corresponding area of the glass pane 3 disposed in front of the light source.

A positioning means 15 with a movable stop is provided along the production line 5 which can be positioned in the transport path of the glass pane 3 and which positions the glass pane 3 in predefined alignment relative to the area light source 14 positioned behind the pane. The targeted illumination of the segment 16 corresponding to the area in the glass pane 3 in which the defect 2 is located can make it significantly easier to locate the defect 2 on the glass pane 3. Depending on the results of a manual check and inspection of the defect 2 in the glass pane 3, the stop of the positioning means 15 can then be relocated out of the transport path of the glass pane 3, allowing the glass pane 3 to be transported further along the production line 5, or the glass pane 3 to be removed from the production process.

Figure 3:
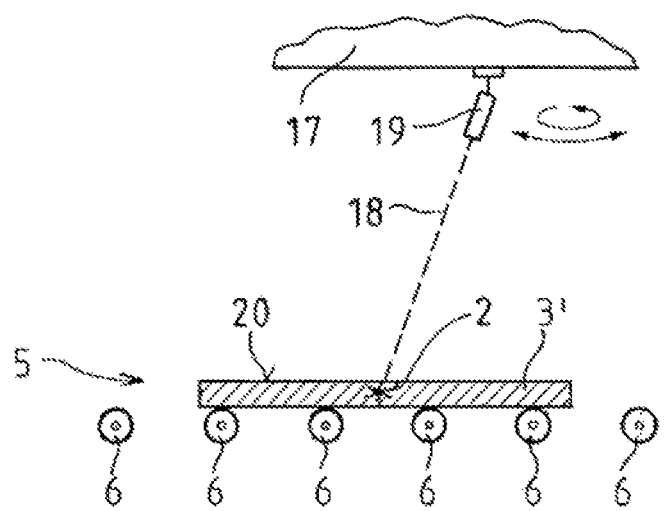

In the exemplary embodiment shown schematically in FIG. 3, a plate-shaped test specimen 3' made of a non-transparent material is transported not upright, but lying flat on the transport rollers 6 along the production line 5. A light source 19 that emits a light beam 18 is mounted on a cover 17 located above the test specimen. The light source 19 can be tipped and pivoted as desired by means of a control device not shown, thereby allowing the illuminated indicator produced by the light beam 18 on a surface 20 of the test specimen 3' to be positioned anywhere on the surface 20. The light source 19 can be suitably controlled to even follow a test specimen 3' moving slowly on the transport rollers 6 under the light source 19, so that the illuminated marking produced on the surface 20 of the test specimen 3' is tracked in correspondence with the defect 2 migrating past the light source 19.

As illustrated in the exemplary embodiments described above, it is possible with a suitable arrangement and alignment of light rails 4, area light sources 14 or pivotable or movable light sources 19 according to an aspect of the invention to provide arbitrarily arranged test specimens 3, 3' with illuminated markings and, in particular, to indicate flaws in glass panes 3 being transported upright or horizontally in production lines 5.

Figure 4:
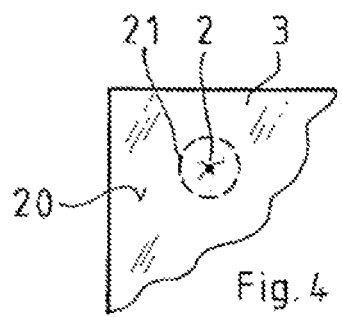
FIG. 4 shows a schematic view of a defect in a glass pane which is localized with a circular illuminated indicator.
Figure 5:
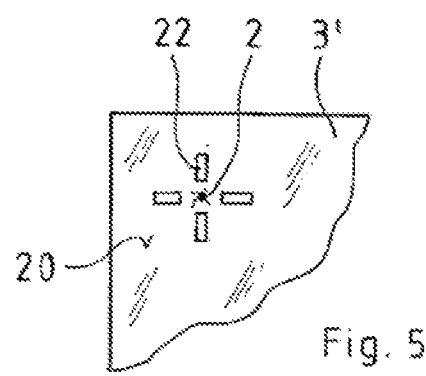
FIG. 5 is a schematic view of a defect in a glass pane which is marked by an illuminated indicator with a different shape.
Figure 6:
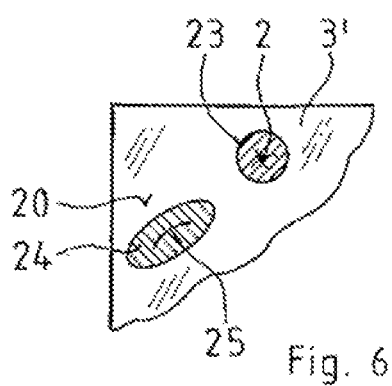
FIG. 6 is a schematic view of two different defects in a glass pane which are marked by two illuminated indicators of varying size and shape.

FIGS. 4 to 6 show examples of different illuminated markings 21, 22, 23 and 24. In the exemplary embodiment shown in FIG. 4, the defect 2 is located on the surface 20 of the test specimen 3' by a circular illuminated marking 21. In the exemplary embodiment shown in FIG. 5 the illuminated marking 22 is in the shape of cross hairs, at the midpoint of which is located the defect 2 on the surface 20 of the test specimen 3'. In the exemplary embodiment as exemplified in FIG. 6 a punctiform defect 2 is marked by a blue-colored circular illuminated marking 23, while an elongated scratch 25 is located by an approximately elliptical, green-colored illuminated marking 24. In this example, the orientation of the illuminated marking 24 corresponds approximately to the progression of the scratch 25, making it that much easier to locate the latter.

The invention claimed is:

1. Method for indicating automatically identified defects on or in a test specimen, comprising
    indicating an identified location of a defect on or in a test specimen by an inspection unit,
    after automatic identification of the defect, checking based on quantifiable properties of the defect whether the test specimen, despite the defect, meets a predefinable quality criterion, and
    subsequent to indicating the location of the defect with the inspection unit, generating an illuminated indicator marking the location of the defect on the surface of the test specimen by a lighting unit behind the test specimen or in the area of at least one adjoining lateral edge of the test specimen only if the quality criterion is not met, the lighting unit being separate from the inspection unit.

2. The method according to claim 1, wherein multiple defects are simultaneously, successively or alternatingly indicated with the marking illuminated indicator.

3. The method according to claim 1, wherein an expansion and/or an orientation of a non-radially symmetrical marking illuminated indicator and/or a coloring of the marking illuminated indicator is predefined depending on the quantifiable properties of the defect.

4. The method according to claim 1, wherein in addition or alternatively, further properties of the test specimen are indicated by the marking illuminated indicator.

5. The method according to claim 1, wherein the marking illuminated indicator is carried along with a moving test specimen.

6. The method according to claim 1, wherein any defects occurring in multiple test specimens transported simultaneously next to one another can be indicated by the marking illuminated indicator.

7. Device for indicating automatically identified flaws on a surface of a test specimen after identification of the flaws by an inspection unit, the device comprising
    the inspection unit for automatically indicating an identified location of a defect on or in the test specimen,
    a positioning means for the test specimen and a lighting unit, the positioning means and the lighting unit being separate from the inspection unit,
    wherein, after automatic identification of the defect and checking whether, based on quantifiable properties of the defect, the test specimen, despite the defect, meets a predefinable quality criterion, the lighting unit is arranged to generate an illuminated indicator marking the location of the defect on the surface or at least at one adjoining lateral edge of the test specimen only if the quality criterion is not met.

8. The device according to claim 7, wherein the lighting unit includes at least one light rail with multiple serially arranged light sources.

9. The device according to claim 8, wherein the lighting unit includes two light rails arranged substantially perpendicular to one another or at an angle to one another, each including multiple serially arranged light sources.

10. The device according to claim 7, wherein the lighting unit comprises an area light source composed of multiple separately controllable segments, the segments corresponding to individual areas of the surface of the test specimen.

11. The device according to claim 10, wherein the test specimen consists of a transparent material and is arranged with its surface directly adjacent to the area light source, such that each area of the surface of the test specimen can be illuminated by a corresponding segment of the area light source.

12. The device according to claim 7, wherein the lighting unit includes at least one pivotable or movable light source arranged at a distance from the test specimen.

13. The device according to claim 12, wherein the light source is arranged to generate an illuminated marking that is predefinable with respect to its shape and size.

14. The device according to claim 12, wherein the light source is arranged to generate an illuminated marking in different colors.

* * * * *